United States Patent
Wang et al.

(10) Patent No.: US 8,844,722 B2
(45) Date of Patent: Sep. 30, 2014

(54) MEDICATION CONTAINER WITH FRESNEL LENS

(76) Inventors: Tom Y. Wang, South Pasadena, CA (US); Richard A. Young, Los Angeles, CA (US); David Truong, Rosemead, CA (US)

(*) Notice: Subject to any disclaimer, the term of this patent is extended or adjusted under 35 U.S.C. 154(b) by 879 days.

(21) Appl. No.: 12/145,355

(22) Filed: Jun. 24, 2008

(65) Prior Publication Data

US 2008/0314786 A1    Dec. 25, 2008

Related U.S. Application Data

(60) Provisional application No. 60/946,133, filed on Jun. 25, 2007.

(51) Int. Cl.
| | | |
|---|---|---|
| *B65D 83/04* | (2006.01) | |
| *G01N 21/01* | (2006.01) | |
| *A61J 1/03* | (2006.01) | |
| *B65D 75/52* | (2006.01) | |

(52) U.S. Cl.
CPC .............. *B65D 75/522* (2013.01); *G01N 21/01* (2013.01); *A61J 1/03* (2013.01); *B65D 2201/00* (2013.01)
USPC .......................................... 206/528; 220/602

(58) Field of Classification Search
USPC .......... 206/528, 534, 535, 540; 359/809, 811, 359/442; 220/602; 215/378, 230
See application file for complete search history.

(56) References Cited

U.S. PATENT DOCUMENTS

| | | | |
|---|---|---|---|
| 1,000,960 A | | 8/1911 | Bell |
| 1,081,210 A | | 12/1913 | Churchill |
| 2,961,108 A | | 11/1960 | Johnson |
| 3,367,484 A | * | 2/1968 | Nelson ........................... 206/540 |
| 3,397,935 A | * | 8/1968 | Michitoshi ..................... 359/413 |
| 3,409,347 A | | 11/1968 | Vogel |
| 3,608,764 A | | 9/1971 | Hedgewick |
| 3,759,411 A | * | 9/1973 | Horvath ......................... 215/209 |
| 3,896,959 A | | 7/1975 | Roy |
| 3,924,772 A | * | 12/1975 | Magnani ........................ 215/276 |
| 3,974,928 A | | 8/1976 | Domaracki et al. |
| 4,044,889 A | | 8/1977 | Orentreich et al. |
| 4,053,078 A | | 10/1977 | Herr |
| 4,057,159 A | | 11/1977 | Fillmore et al. |

(Continued)

FOREIGN PATENT DOCUMENTS

| | | | | |
|---|---|---|---|---|
| DE | 4133798 A1 | * | 4/1992 | ............ B65D 25/54 |
| JP | 2003-202300 | | 7/2003 | |
| WO | 01-94894 A1 | | 12/2001 | |

OTHER PUBLICATIONS

Abstract of DE 4133798 A1.*

(Continued)

*Primary Examiner* — David Fidei
(74) *Attorney, Agent, or Firm* — Chen Yoshimura LLP

(57) ABSTRACT

A medication container with a Fresnel lens formed on its surface is described. The Fresnel lens provides a magnified view of the medication content of the container so that a user such as a pharmacist or a patient can accurately determine the medication content without opening the container. In one embodiment, the medication container is generally cylindrical in shape and a Fresnel lens is formed on the bottom of the container. In other embodiments, the Fresnel lens is formed on the cap of a middle component located between the cap and the body of the container.

4 Claims, 7 Drawing Sheets

(56) References Cited

U.S. PATENT DOCUMENTS

| | | | |
|---|---|---|---|
| 4,059,198 A | | 11/1977 | Mumford |
| 4,119,232 A | * | 10/1978 | Thornton ...................... 215/222 |
| 4,609,259 A | * | 9/1986 | Suemitsu et al. ............... 355/53 |
| 4,747,499 A | * | 5/1988 | Gach et al. ..................... 215/250 |
| 4,747,500 A | * | 5/1988 | Gach et al. ..................... 215/250 |
| 4,784,258 A | * | 11/1988 | Figari ............................ 206/5.1 |
| 4,877,143 A | | 10/1989 | Travisano |
| 5,064,082 A | | 11/1991 | Lombardi et al. |
| 5,400,915 A | * | 3/1995 | Kennedy ....................... 220/377 |
| 5,760,975 A | * | 6/1998 | DiGiovanni .................. 359/802 |
| 5,896,686 A | * | 4/1999 | Howes ............................ 40/311 |
| 6,036,017 A | * | 3/2000 | Bayliss, IV ................... 206/534 |
| 6,199,710 B1 | * | 3/2001 | Jensen .......................... 215/228 |
| 6,278,545 B1 | | 8/2001 | Napier |
| 6,386,367 B1 | | 5/2002 | Bayliss |
| 6,450,343 B1 | * | 9/2002 | Arnaldi ......................... 206/769 |
| 6,594,928 B1 | * | 7/2003 | Clawson et al. ................ 40/310 |
| 6,621,629 B2 | | 9/2003 | Blumenthal et al. |
| 2005/0252877 A1 | * | 11/2005 | Moller .......................... 215/222 |
| 2006/0171044 A1 | * | 8/2006 | Carnevali ...................... 359/802 |

OTHER PUBLICATIONS bhlens.com, Manufacturer of the Fresnel Lens, copyright © 2006.*
International Search Report and Written Opinion in counterpart PCT application No. PCT/US2008/068055, dated Oct. 2, 2008.

* cited by examiner

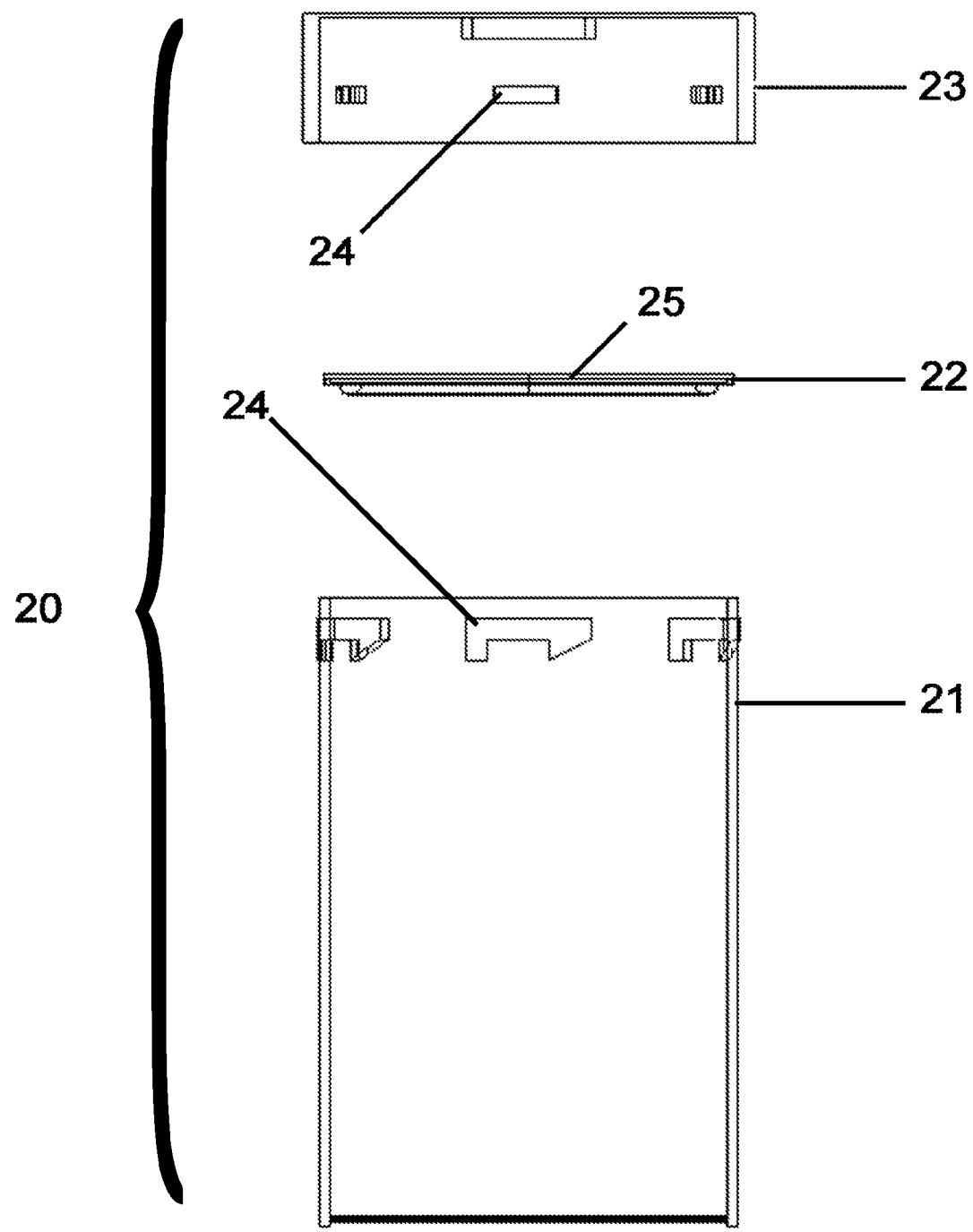

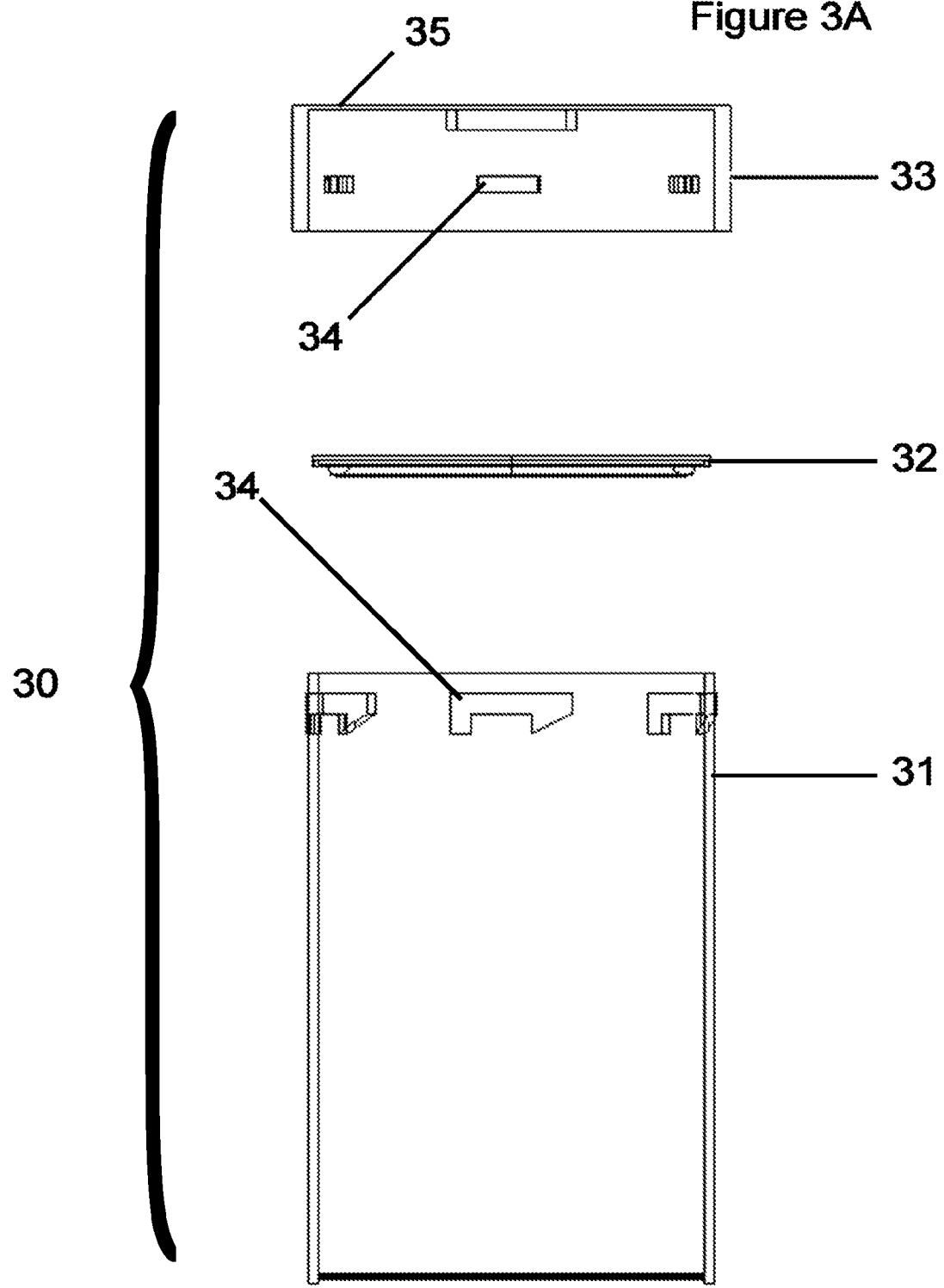

15/25/35

MEDICATION CONTAINER WITH FRESNEL LENS

This application claims priority from U.S. Provisional Patent Application No. 60/946,133, filed Jun. 25, 2007, which is herein incorporated by reference in its entirety.

BACKGROUND OF THE INVENTION

1. Field of the Invention

This invention relates to medication containers used for dispensing medications in pharmacies and healthcare settings.

2. Description of the Related Art

At a pharmacy which fills medication prescriptions, a main function of a pharmacist is to ensure that the correct medication is given to the correct patient, thus ensuring patient safety. Due to the increasing number of prescriptions written by medical providers, there has been a shortage in resources to support the overwhelming need to dispense the large number of prescription medications. There has also been a need for more efficient prescription processing and filling turnover to fulfill the increased demand. To meet the aforementioned increases in prescriptions, demand and desire to provide better patient service, the pharmacy industry has strived to increase efficiency and speed. However, the resulting increases in efficiency and speed may lead to compromised medication filling accuracy and increased medication filling errors. Consequently, patient safety may be grossly affected.

With the rise in the number of prescriptions written and filled, patients are being exposed to more and more dangerous medications. Medications are becoming more potent and the small, hard to read features on medications do not allow for easy identification. Unfortunately, due to the high volume of prescriptions filled daily, pharmacists and pharmacy personnel are making mistakes. Combined with difficulty to distinguish one pill from another, patients often ingest the wrong medication through the mistakes of either the pharmacy or by the patients themselves. These medication errors contribute to the increase in poisonings, life threatening injuries and fatalities in patients.

Additionally, with the large volume of prescriptions being filled, pharmacists and pharmacy personnel are faced with the repetitive motion of opening and closing prescription containers to identify and verify the medication given to the patients during the review stage of the filling workflow. The repetitive motion of opening and closing has become a source of occupational injuries for pharmacy personnel leading to decreased productivity and increased costs in work related injury costs.

The current state of pharmacy operations for dispensing medications has numerous problems that lead to increases in healthcare dollars associated with preventable wrong-medication ingestion injuries, repetitive motion injuries, suffering and expenditures for both employers and patients. Therefore, there is a need to have products or tools to improve efficiency, to meet the increased demand, and to prevent work related injuries without compromising patient safety.

U.S. Pat. Nos. 6,036,017 and 6,386,367 describe a safety prescription container that includes a cylindrical receptacle, a detachable cap, and a label. A pill holder is positioned beneath the cap, which includes a magnifying lens (a convex lens), through which the interior of the pill holder can be viewed (see FIGS. 2 and 3 thereof). Another embodiment (FIG. 4 thereof) includes a magnifying lens (a convex lens) located at the bottom of the container.

SUMMARY OF THE INVENTION

The present invention is directed to medication container that substantially obviates one or more of the problems due to limitations and disadvantages of the related art.

An object of the present invention is to provide a medication container that addresses the above-discussed problems thereby reducing mistakes, improving pharmacy workflow efficiency, enhancing safety, reducing occupational injuries and promoting patient wellbeing.

Another object of the present invention is to provide a medication container that helps ensure the safety of a growing patient population reliant on medications by making the identification of medications easier for patients.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, the present invention provides a medication container which includes a container body having a flat bottom panel with a Fresnel lens formed thereon and a cap for engaging the container body.

In another aspect, the present invention provides a container which includes a container body and a closing member for engaging the container body, wherein a Fresnel lens is formed on a surface of either the container body or the closing member.

It is to be understood that both the foregoing general description and the following detailed description are exemplary and explanatory and are intended to provide further explanation of the invention as claimed.

BRIEF DESCRIPTION OF THE DRAWINGS

FIGS. 2A and 2B are an exploded cross-sectional view and an exploded perspective view, respectively, of a medication container according to a second embodiment of the present invention.

FIGS. 3A and 3B are an exploded cross-sectional view and an exploded perspective view, respectively, of a medication container according to a third embodiment of the present invention.

DETAILED DESCRIPTION OF THE PREFERRED EMBODIMENTS

Various embodiments of the present invention provide a medication container with a Fresnel lens that allows for a magnified view of the medication contents (e.g. pills) in the container so that their imprint, score, color, shape, and design are clear and obvious to pharmacists and patients. One embodiment of the invention (FIGS. 1A and 1B) is a medication container with a Fresnel lens formed at the base (bottom) of the container. A variation of this embodiment (not shown in the figures) is a medication container with a Fresnel lens formed on a planar side wall of the container. A second embodiment (FIGS. 2A and 2B) is a medication container having a Fresnel lens formed as a middle piece placed between the cap and the interior of the container. A third embodiment (FIGS. 3A and 3B) is a medication container having a Fresnel lens integrated into the cap.

Figure 1A:
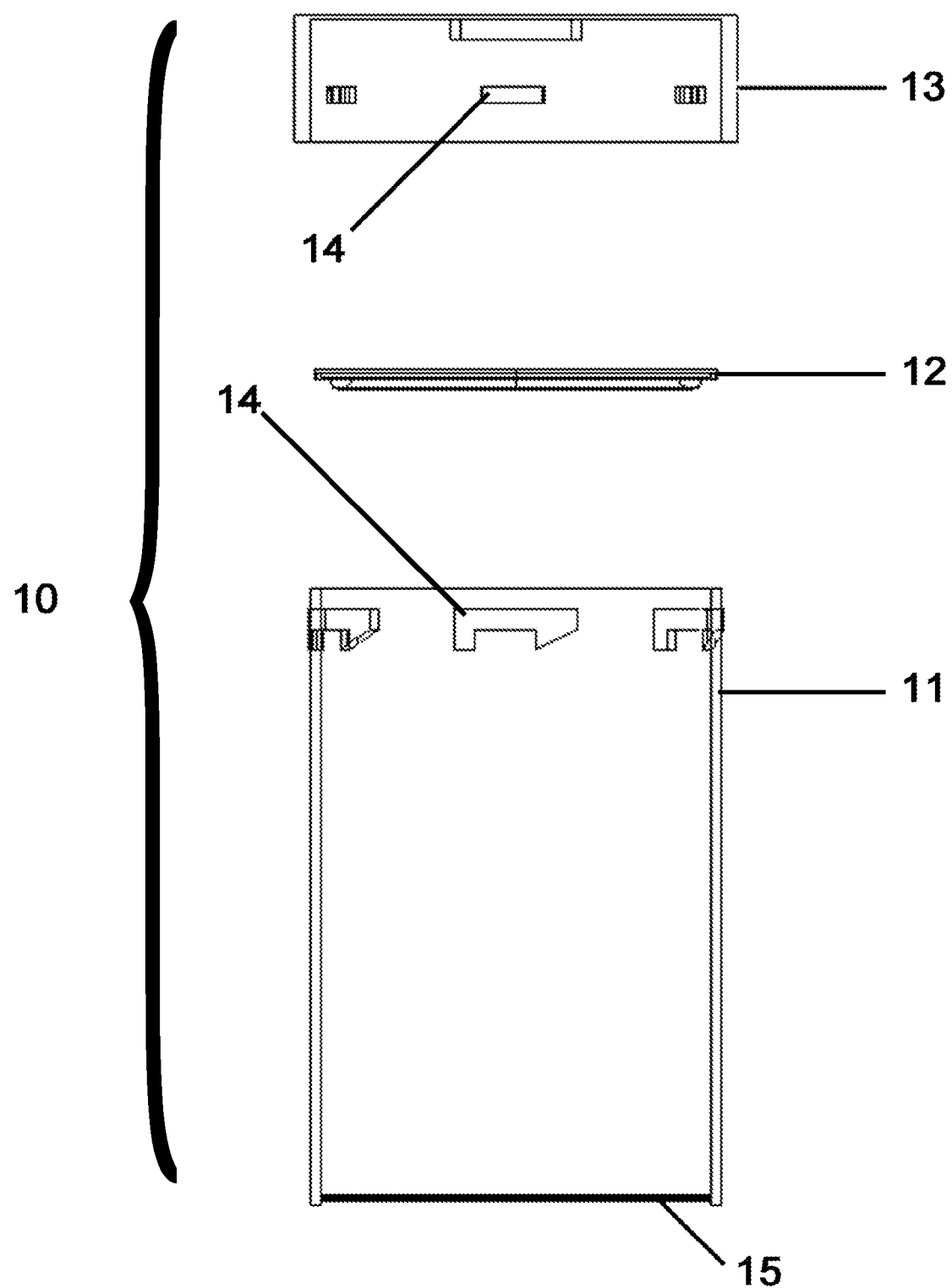
FIGS. 1A and 1B are an exploded cross-sectional view and an exploded perspective view, respectively, of a medication container according to a first embodiment of the present invention.
Figure 1B:
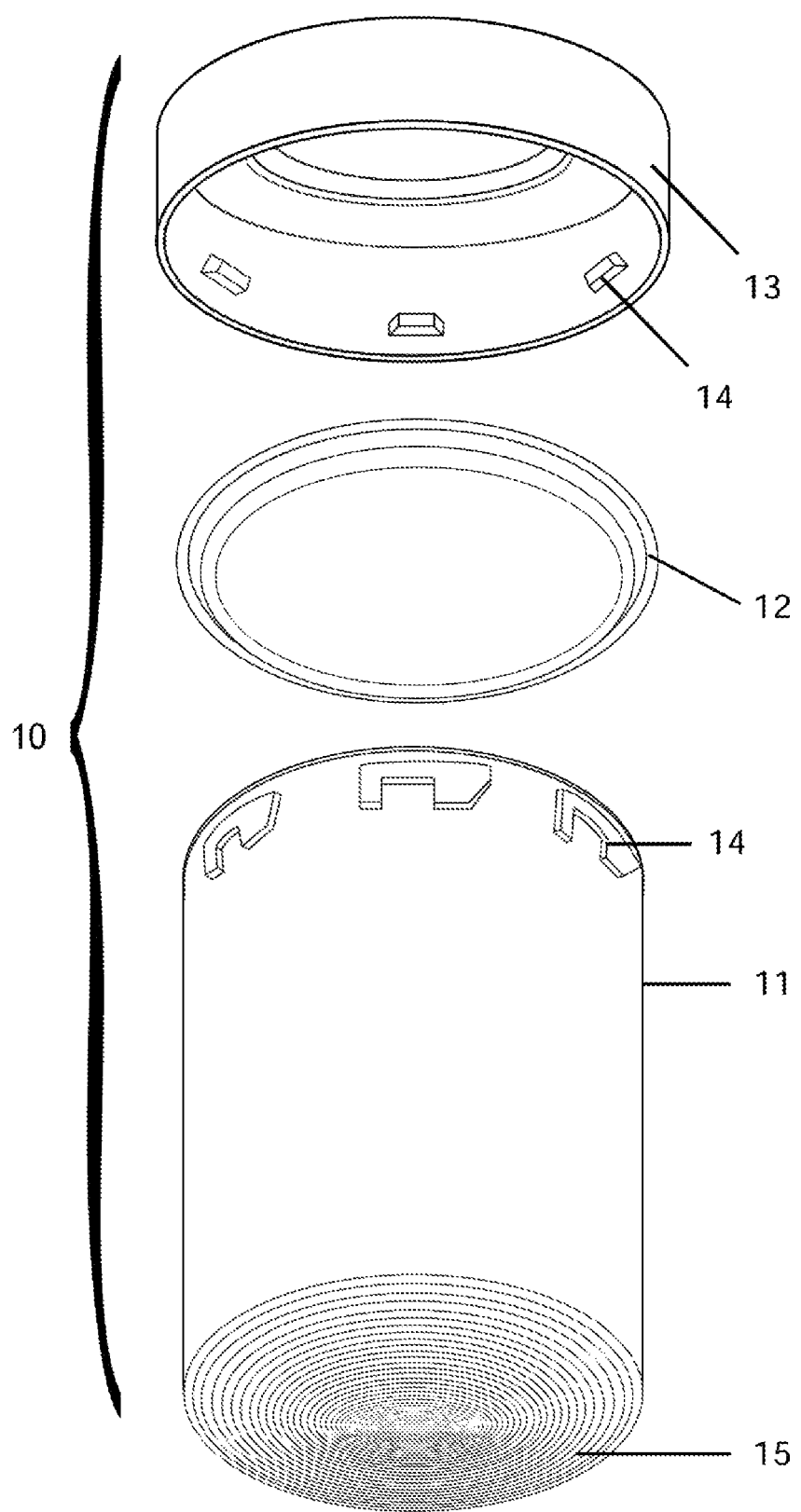

FIG. 1A is an exploded cross sectional view of a medication container 10 according to the first embodiment, and FIG. 1B is an exploded perspective view thereof. The medication container 10 includes a body 11, a cap 13, and a middle component 12 such as a seal, a barrier, or the like disposed between the cap and the body. In the illustrated embodiment, the body 11 has a generally cylindrical shape, but other shapes may also be used. The cap 13 and the body 11 are designed to engage each other in a threaded or non-threaded manner. Preferably, a child proof mechanism 14 is provided within the interior of the cap and on the body. Child proof mechanisms for medication containers are well known in the art. Alternatively, the cap 13 may be an easy to remove caps often used by elderly patients. Typically, the middle component 12 is retained in the cap 13 when the cap is removed from the container body 11. A Fresnel lens 15 is formed on a bottom panel of the container body 11 opposite to the opening.

As a variation of the first embodiment (not shown in the drawings), the body 11 of the container has a planar side wall, and a Fresnel lens is formed on the planar side wall.

Figure 4:
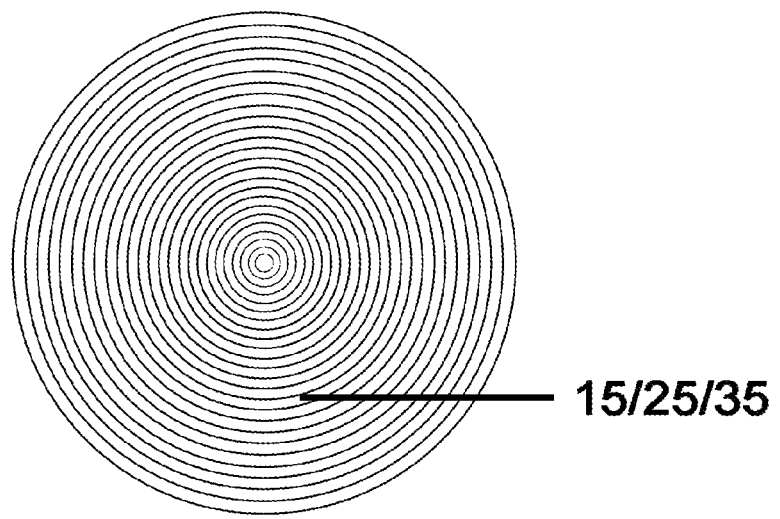
FIG. 4 is a plan view of the Fresnel lens used in the medication containers of FIGS. 1A-3B.

FIG. 4 is a plan view illustrating a Fresnel lens. A Fresnel lens is a non-conventional optical formation consisting of concentric circular prism rings that can function as a magnifier. One type of Fresnel lens is commonly available as a light-weight hand-held magnifier, for example, for reading. This type of Fresnel lens is made of a transparent material having an apparently flat surface with fine grooves formed thereon. The Fresnel lens formation in the above embodiment is design to provide magnification from 1× to 10× (or any other desired or suitable magnification), depending on the desired magnification needed for the various medication container sizes and applications. When using the Fresnel lens in the medication container 10 shown in FIGS. 1A and 1B, the container may be tilted at a desired angle or turned upside-down so that the Fresnel lens faces upwards, allowing easy viewing of an enlarged view of the contents of the container.

Figure 2B:
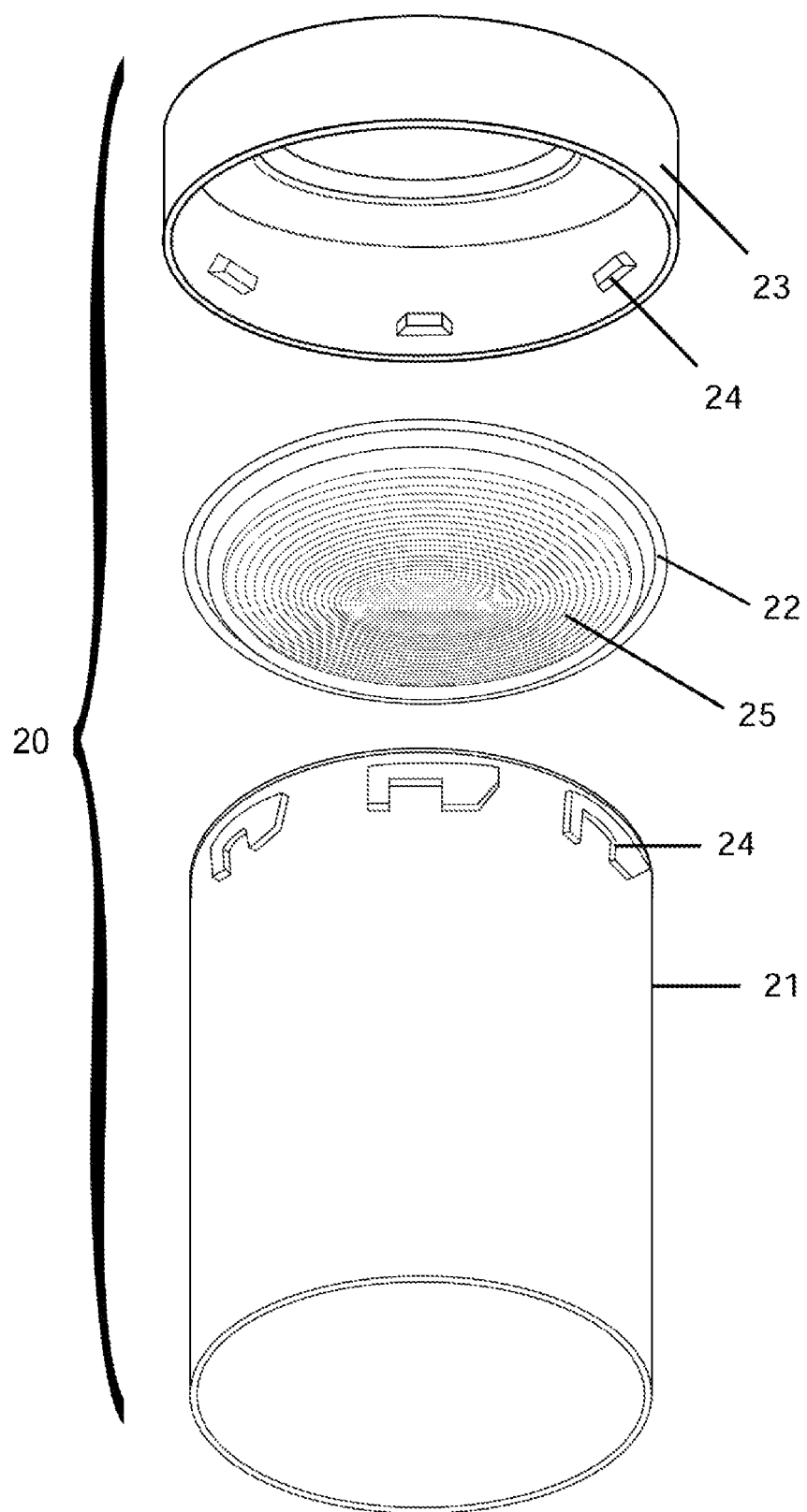

FIG. 2A is an exploded cross sectional view of a medication container 20 according to the second embodiment, and FIG. 2B is an exploded perspective view thereof. The medication container 20 includes a body 21, a cap 23, and a middle component 22 such as a seal, a barrier, or the like disposed between the cap and the body. A child proof mechanism 24 may be provided on the cap 23 and the body 21. A Fresnel lens 25 is combined with the middle piece 22 as a part thereof, such that the Fresnel lens 25 is located near the top of the container body 21 when the cap is closed. Preferably, the Fresnel lens 25 is an integral part of the middle component 22. In this embodiment, the cap 23 has a transparent face to allow viewing of the contents of the container through the Fresnel lens 25 when the cap is closed. Unlike the first embodiment, the container 20 of the second embodiment does not need to be turned upside-down for viewing of the contents.

Figure 3B:
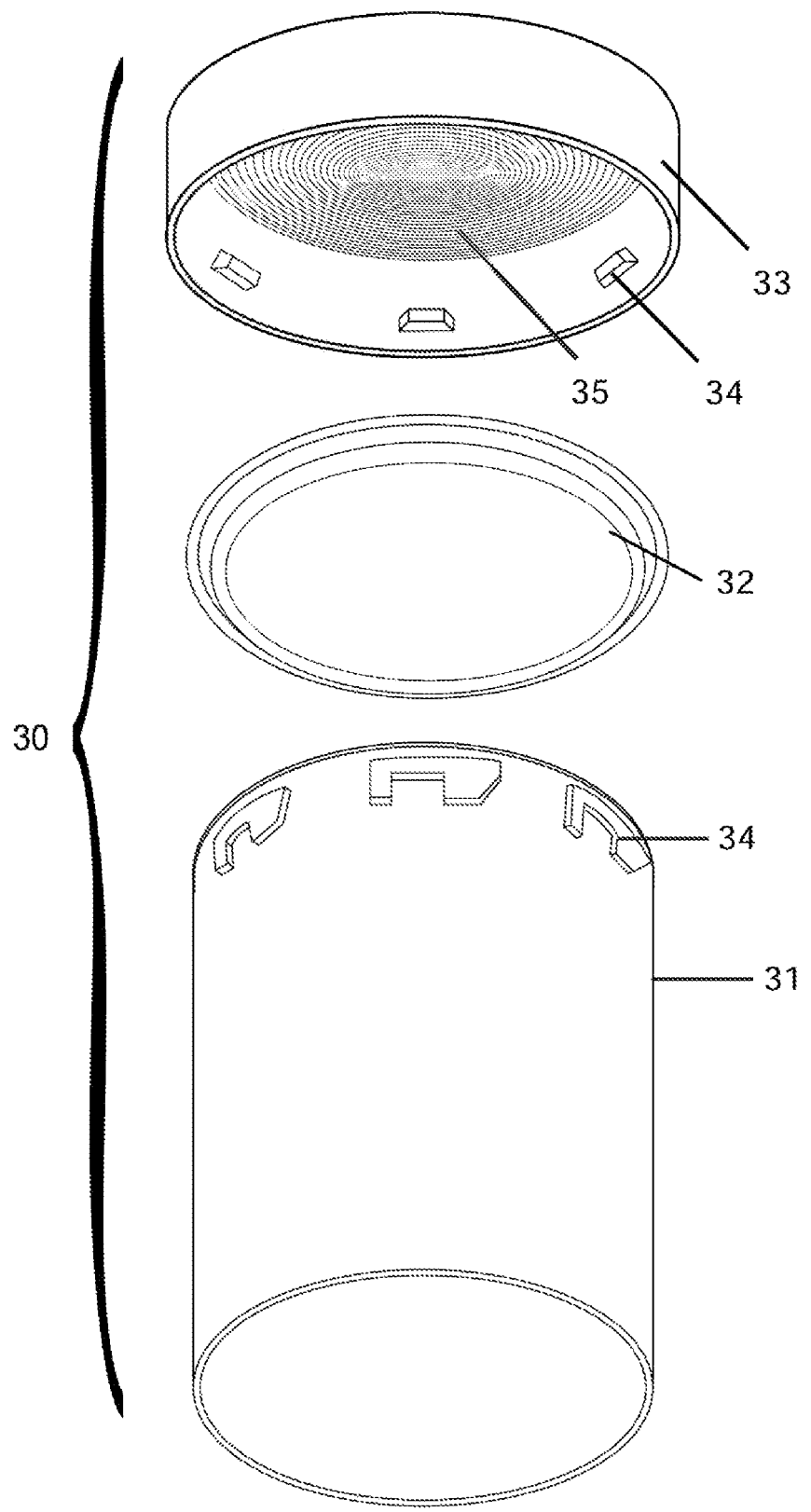

FIG. 3A is an exploded cross sectional view of a medication container 30 according to the third embodiment, and FIG. 3B is an exploded perspective view thereof. The medication container 30 includes a body 31, a cap 33, and a middle component 32 such as a seal, a barrier, or the like disposed between the cap and the body. A child proof mechanism 34 may be provided on the cap 33 and the body 31. A Fresnel lens 35 is combined with the cap 33 as a part thereof. Preferably, the Fresnel lens 35 is an integral part of the cap 33. In this embodiment, the middle piece 32 either has a transparent face or has an opening in the center area to allow viewing of the contents of the container through the Fresnel lens 35.

The middle component 12/22/32 of the medication container may be generally considered to be a part of a closing member (cap) of the container. Thus, in the second and third embodiments the Fresnel lens can be considered to be formed on the cap.

In the above three embodiments, except for the incorporation of the Fresnel lenses, the container body, the cap and the middle component of the medication container are otherwise commonly used components for medication containers. Such medication container with Fresnel lens may be manufactured by modifying conventional methods of manufacturing medication containers. The Fresnel lens and the rest of the container are made from plastic or other materials that are compatible for use with medications. The material also possesses UV (ultraviolet) protection properties. The medication container and the cap are typically made by a process of plastic injection molding and/or blow molding well known in the art. Thermoplastics and thermosetting plastic materials such as polypropylene (PP) are typically used in these molding processes.

A preferred way of making a medication container with a Fresnel lens incorporated at the bottom of the container (the first embodiment) is to form the entire container body as one piece from a molding process. The mold for the container body has a Fresnel lens formation for the bottom panel. Fabrication of such mold is within the knowledge and ability of persons skilled in the art of making Fresnel lenses and in mold design and mold tooling/machining. For example, the Fresnel lens formation at the bottom of the mold may be tooled by using a laser cutting directly onto the inner cavities of the metal mold. As the plastic material is injected into the mold, the base of the mold corresponding to the bottom panel of the container is cooled first by a suitable coolant. This step reduces or eliminates distortions that may occur with the lens when the formed medication container is extracted from the mold. Then, the rest of the mold is cooled by a coolant to solidify the rest of the medication container.

Many polypropylene materials available from various manufacturers were researched in order to determine suitable polypropylenes for the medication container with Fresnel lens. The polypropylene specification for this application requires a high degree of clarity when it is in its solid form. The polypropylene should also be non-reactive, chemical resistant, and non-leaching. Preferably, the polypropylene is also suitable for adding desired color pigmentations and UV resistant materials without significantly affecting its desired physical properties. The following is a list of polypropylene products that may be used for the medication container with Fresnel lens: PP9074MED made by ExxonMobil Chemical; Pro-Fax ST757M made by Basell Polyolefins; TR3350C made by Sunoco Chemical; and YungSox 5350T, YungSox 5090T and YungSox 5060T made by Formosa Polypropylene. Of course, many other polypropylene or other plastic materials, including those that may become available in the future, may also be suitable for this application. Suitable color pigmentations and UV resistant materials may be added to the PP material.

An alternative way of making a medication container with a Fresnel lens incorporated on the bottom panel of the container (the first embodiment) is to form the bottom panel (the Fresnel lens) separately from the rest of the body of the container, and join them together. The Fresnel lens and the rest of the container body may use different materials.

A cap or a middle component for a medication container incorporating a Fresnel lens (second and third embodiment)

may be manufactured by similar processes as described above. Of course, other suitable manufacturing processes may be used to make the medication container with Fresnel lens described above, including processes that will become available in the future.

Unlike the medication container shown in FIG. 4 of U.S. Pat. Nos. 6,036,017 and 6,386,367, the medication containers according to embodiments of the present invention do not rely on a conventional convex lens for magnification. It is an optical formation consisting of concentric circular prism rings. As a result, a transverse support base for the pills required by the prior medication container for proper magnification can be eliminated. Further, the prior container requires the user to keep the container upright so that the pills are located at a predetermined distance from the magnifying lens, and raise the container and look upwards through the magnifying lens at the bottom of the container. The medication containers according to embodiments of the present invention are more convenient to use as the user can look down through the Fresnel lens. By using a properly designed Fresnel lens, desired magnification can be achieved for objects located anywhere in the container. This allows the viewer to magnify the contents at a tilted, semi-inverted, or inverted position without having to raise the container in an upright position and look through the lens from the bottom.

Medication containers according to embodiments of the present invention allow for increased ease and accuracy of reading imprints, viewing of pill color, pill shape, and score design without opening the bottle. Thereby, upon comparison with the description of the medication, mistakes can be avoided. This improves the safety of patients by minimizing mistakes when medications look similar. It also increases efficiency by reducing the time it takes for the pharmacist to complete the final verification process because they will not have to open the container as often to perform their final shape/color/imprint check. It minimizes the need for unnecessary repetitive motion of opening the container thereby reducing the injuries of the hand, wrist, and arm that are a common occupational hazard associated with the pharmacy profession. Medication containers according to embodiments of the present invention also provide an added safety feature for patients to identify their medication correctly since the contents are magnified to show detail of the pill color, shape, and score design without opening the bottle. It adds a convenience factor for patients since they will not need to open the bottles to identify which pill they are supposed to take.

The Fresnel lens can be made in various sizes and be attached to various sizes and shapes of medication containers. The illustrated embodiments show the Fresnel lens being located at the bottom or top of a cylindrical shaped container, but more generally, the Fresnel lens may be located on any suitable surface of the container.

Fresnel lenses may be used on various types of medication containers that are commonly used in mail order pharmacies and automated refill machines, or any other suitable types of medication containers. More generally, Fresnel lenses may be used as containers for objects other than medication. The invention is not limited by the particular intended use of the container, although as currently contemplated its main use will be medication containers for dispensing medications in pharmacies and healthcare settings.

It will be apparent to those skilled in the art that various modification and variations can be made in the medication containers of the present invention without departing from the spirit or scope of the invention. Thus, it is intended that the present invention cover modifications and variations that come within the scope of the appended claims and their equivalents.

What is claimed is:

1. A medicine container comprising:
a container body; and
a closing member for engaging the container body, wherein the closing member includes a cap and a middle component disposed between the cap and the container body forming a seal or barrier, and wherein a Fresnel lens is formed on the middle component for magnifying a content within the container.

2. The medication container of claim 1, wherein the container body is formed of a plastic material.

3. The medication container of claim 2, wherein the container body is formed of a polypropylene material by injection molding.

4. The medication container of claim 2, wherein the plastic material has ultraviolet protection properties.

* * * * *